US012576021B2

(12) United States Patent
O'Connor et al.

(10) Patent No.: US 12,576,021 B2
(45) Date of Patent: Mar. 17, 2026

(54) METHOD OF MAKING AND USING A SKIN MOISTURIZING FORMULATION

(71) Applicants: Rohm and Haas Company, Collegeville, PA (US); Dow Silicones Corporation, Midland, MI (US); Union Carbide Corporation, Seadrift, TX (US)

(72) Inventors: Ying O'Connor, Coatesville, PA (US); Emmett M. Partain, III, Bound Brook, NJ (US); Lyndsay M. Leal, Spring City, PA (US); Jennifer P. Todd, Willow Grove, PA (US); Sokhomari S. Suon, Ardmore, PA (US); Anne-Marie Vincent, Seneffe (BE)

(73) Assignees: Rohm and Haas Company, Collegeville, PA (US); Dow Silicones Corporation, Midland, MI (US); Union Carbide Corporation, Seadrift, TX (US)

( * ) Notice: Subject to any disclaimer, the term of this patent is extended or adjusted under 35 U.S.C. 154(b) by 551 days.

(21) Appl. No.: 17/923,465

(22) PCT Filed: Jun. 18, 2021

(86) PCT No.: PCT/US2021/037973

§ 371 (c)(1),
(2) Date: Nov. 7, 2022

(87) PCT Pub. No.: WO2021/262536

PCT Pub. Date: Dec. 30, 2021

(65) Prior Publication Data

US 2023/0190622 A1 Jun. 22, 2023

Related U.S. Application Data

(60) Provisional application No. 63/042,774, filed on Jun. 23, 2020.

(51) Int. Cl.

*A61K 8/73* (2006.01)
*A61Q 17/04* (2006.01)
*A61Q 19/00* (2006.01)

(52) U.S. Cl.

CPC ................ *A61K 8/73* (2013.01); *A61Q 17/04* (2013.01); *A61Q 19/007* (2013.01)

(58) Field of Classification Search

CPC ......... A61K 8/73; A61Q 17/04; A61Q 19/007
USPC ........................................................... 514/59
See application file for complete search history.

(56) References Cited

U.S. PATENT DOCUMENTS

| | | | | |
|---|---|---|---|---|
| 4,411,891 | A | 10/1983 | Mizutani et al. | |
| 8,796,196 | B2 * | 8/2014 | Chan | C08B 37/0096 510/330 |
| 9,351,910 | B2 * | 5/2016 | Chen | A61K 8/11 |
| 2005/0227902 | A1 | 10/2005 | Erazo-Majewicz et al. | |
| 2008/0213199 | A1 | 9/2008 | Philippe | |
| 2012/0295983 | A1 | 11/2012 | Au et al. | |

FOREIGN PATENT DOCUMENTS

| | | | |
|---|---|---|---|
| CN | 109157451 | A | 1/2019 |
| FR | 2903000 | A1 | 1/2008 |
| JP | 2000159642 | A | 6/2000 |
| JP | 4712222 | B2 | 6/2011 |
| WO | 2021194806 | A1 | 9/2021 |
| WO | WO 2021/194804 | * | 9/2021 |

OTHER PUBLICATIONS

Sibilia, "A Guide to Materials Characterization and Chemical Analysis", VCH, 1988, pp. 81-84.
Yau, Modern Size Exclusion Chromatography, Wiley-Interscience, 1979.

* cited by examiner

*Primary Examiner* — Yih-Horng Shiao
(74) *Attorney, Agent, or Firm* — Thomas S. Deibert

(57) ABSTRACT

A method for making a skin moisturizing formulation is provided, comprising: providing a dermatologically acceptable vehicle; selecting a skin moisturizing agent based on its ability to absorb and retain moisture, wherein the skin moisturizing agent selected is a cationic dextran polymer, comprising a dextran polymer functionalized with quaternary ammonium groups; providing the selected skin moisturizing agent; combining the dermatologically acceptable vehicle and the skin moisturizing agent to form a skin moisturizing formulation; wherein the skin moisturizing formulation contains 0.05 to 10 wt %, based on weight of the skin moisturizing formulation, of the skin moisturizing agent. Also provided is a method for moisturizing skin.

2 Claims, No Drawings

METHOD OF MAKING AND USING A SKIN MOISTURIZING FORMULATION

The present invention relates to a method for making a skin moisturizing formulation. In particular, the present invention relates to a method for making a skin moisturizing formulation, comprising: providing a dermatologically acceptable vehicle; selecting a skin moisturizing agent based on its ability to absorb and retain moisture, wherein the skin moisturizing agent selected is a cationic dextran polymer, comprising a dextran polymer functionalized with quaternary ammonium groups; providing the selected skin moisturizing agent; combining the dermatologically acceptable vehicle and the skin moisturizing agent to form a skin moisturizing formulation; wherein the skin moisturizing formulation contains 0.05 to 10 wt %, based on weight of the skin moisturizing formulation, of the skin moisturizing agent.

Moisturizing ingredients are a key ingredient in many skin care formulations because most consumers suffer from dry skin to some degree. Good moisturizers can provide a reduction in itchy and dry skin, decrease skin irritation and slow down the aging process. There are two general classes of materials employed to combat skin dryness—occlusives and humectants. Occlusives, such as petrolatum and silicone oils, serve to inhibit loss of skins natural moisture by forming a barrier between the epidermis and the surrounding environment. Humectants, which are hygroscopic substances that form hydrogen bonds with water molecules, help to hydrate skin by attracting water molecules to the skin from the environment, thus moisturizing dry skin.

Among commonly used humectants, hyaluronic acid and sodium hyaluronate a biopolymer found in connective, epithelial and neural mammalian tissues. Hyaluronic acid is a high molecular weight (1,000 KDa to 3,000 KDa), anionic polysaccharide that is composed of repeating disaccharide units of D-glucuronic acid and n-acetyl-D-glucosamine Compared to other humectants, hyaluronic acid is less affected by the environment. Due to its highly hygroscopic nature (it is capable of absorbing 1,000 times its weight in water) and its non-greasy feel, hyaluronic acid is one of the most popular and highly desired humectants for skin care formulations. Nevertheless, due to its high cost the use of hyaluronic acid is limited to high-end skin care leave-on products.

One alternative type of skin moisturization material is disclosed by Au et al. in U.S. Patent Application Publication No. 20120295983. Au et al teach a composition comprising a cationic ammonium compound and a metal chelator, the metal chelator being one which impedes the generation of a nitrogen comprising group from the cationic ammonium compound within the composition.

Notwithstanding, there remains a continuing need for effective, lower cost moisturizing materials useful in skin care formulations.

The present invention provides a method for making a skin moisturizing formulation, comprising: providing a dermatologically acceptable vehicle; selecting a skin moisturizing agent based on its ability to absorb and retain moisture, wherein the skin moisturizing agent selected is a cationic dextran polymer, comprising a dextran polymer functionalized with quaternary ammonium groups; providing the selected skin moisturizing agent; combining the dermatologically acceptable vehicle and the skin moisturizing agent to form a skin moisturizing formulation; wherein the skin moisturizing formulation contains 0.05 to 10 wt %, based on weight of the skin moisturizing formulation, of the skin moisturizing agent.

The present invention provides a skin moisturizing formulation prepared according to the method of the present invention.

The present invention provides a method for moisturizing skin, comprising: providing a skin moisturizing formulation prepared according to the method of the present invention; and applying the skin moisturizing formulation to the skin of a mammal.

DETAILED DESCRIPTION

We have surprisingly found an effective method for making a skin moisturizing formulation, wherein the skin moisturizing formulation produced comprises a skin moisturizing agent and wherein the skin moisturizing agent is selected based on its ability to absorb and retain moisture.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and dextran standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p.81-84. Molecular weights are reported herein in units of Daltons, or equivalently, g/mol.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the skin moisturizing formulation prepared by the method of the present invention is selected from the group consisting of a leave-on formulation and a rinse-off formulation. More preferably, the skin moisturizing formulation prepared by the method of the present invention is selected from the group consisting of a lotion (e.g., a moisturizing lotion), a cream (e.g., a blemish balm cream, a dynamic do-all cream, an anti-wrinkle cream), a serum, a gel, a gel cream, a roll-on formulation, a stick, a mousse, a spray (aerosol or non-aerosol), a fabric or a wipe (e.g., nonwoven textile applied formulation, a toner, a mask, a sunscreen, a color cosmetic, a foundation, a powder, an antiperspirant, a lipstick, a lip gloss, a deodorant, a baby care formulation, a hand sanitizer, a hand soap, a body wash, a facial wash and a soap bar. Most preferably, the skin moisturizing formulation prepared by the method of the present invention is a leave-on formulation selected from the group consisting of a color cosmetic, a sunscreen, a lotion and a cream.

Preferably, the method of making a skin moisturizing formulation of the present invention comprises: providing a dermatologically acceptable vehicle; selecting a skin moisturizing agent based on its ability to absorb and retain moisture, wherein the skin moisturizing agent selected is a cationic dextran polymer, comprising a dextran polymer functionalized with quaternary ammonium groups; providing the selected skin moisturizing agent; combining the dermatologically acceptable vehicle and the skin moisturizing agent to form a skin moisturizing formulation; wherein the skin moisturizing formulation contains 0.05 to 10 wt %, based on weight of the skin moisturizing formulation, of the skin moisturizing agent. Preferably, the ability of the skin moisturizing agent to absorb and retain moisture is determined based on the experimental procedure set forth herein in the Examples.

Preferably, the method of making a skin moisturizing formulation of the present invention comprises providing a dermatologically acceptable vehicle; wherein the dermatologically acceptable vehicle includes at least one of water, an emollient, a fatty acid, a fatty alcohol, a thickener and combinations thereof. More preferably, the method of making a skin moisturizing formulation of the present invention comprises providing a dermatologically acceptable vehicle; wherein the dermatologically acceptable vehicle includes at least one of water, an emollient, a fatty acid, a fatty alcohol, a thickener and combinations thereof; wherein the dermatologically acceptable vehicle is in the form of an emulsion, a cream, an aqueous solution, an oil, an ointment, a paste, a gel, a lotion, a milk, a foam, a suspension and a powder. Most preferably, the method of making a skin moisturizing formulation of the present invention comprises providing a dermatologically acceptable vehicle; wherein the dermatologically acceptable vehicle includes at least one of water, an emollient, a fatty acid, a fatty alcohol, a thickener and combinations thereof; wherein the dermatologically acceptable vehicle is in the form of an emulsion, a cream, an aqueous solution, an oil, an ointment, a gel, a lotion, a milk, a foam and a suspension.

Preferably, the method of making a skin moisturizing formulation of the present invention, comprises providing a dermatologically acceptable vehicle; wherein the skin moisturizing formulation formed contains 1 to 99.95 wt % (preferably, 70 to 95 wt %; more preferably, 80 to 90 wt %), based on weight of the skin moisturizing formulation, of the dermatologically acceptable vehicle.

When the dermatologically acceptable vehicle provided includes water, the skin moisturizing formulation formed will preferably contain 5 to 95 wt % (preferably, 20 to 70 wt %; more preferably, 35 to 60 wt %), based on weight of the skin moisturizing formulation, of water.

Preferably, the dermatologically acceptable vehicle provided includes an emollient, the emollient materials used may be in the form of silicone oils, natural or synthetic esters and hydrocarbons. Preferably, when the dermatologically acceptable vehicle provided includes an emollient, the skin moisturizing formulation formed will preferably contain 0.1 to 95 wt % (more preferably, 1 to 50 wt %), based on weight of the skin moisturizing formulation, of emollient.

Silicone oils may be separated into volatile silicones and nonvolatile silicones. Volatile silicone oils are those silicones which have a measurable vapor pressure at ambient temperature. Such volatile silicone oils are preferably selected from cyclic (cyclomethicone) or linear polydimethylsiloxanes which contain from 3 to 9 (preferably, 4 to 5) silicone atoms per molecule. Nonvolatile silicone oils include polyalkyl siloxanes, polyalkylaryl siloxanes and polyether siloxane copolymers. Such nonvolatile silicone oils include, for example, polydimethylsiloxanes having viscosities of $5\times10^{-6}$ to 0.1 $m^2/s$ at 25° C. (preferably, $1\times10^{-5}$ to $4\times10^{-4}$ $m^2/sec$ at 25° C.). Another class of nonvolatile silicones are emulsifying and nonemulsifying silicone elastomers (e.g., Dimethicone/Vinyl Dimethicone Crosspolymer available from Dow Silicones). Yet another class of nonvolatile silicones are waxes (e.g., Dimethicone PEG-8 Laurate).

Ester emollients may include: (i) alkyl esters of saturated fatty acids having 10 to 24 carbon atoms (e.g., behenyl neopentanoate, isononyl isonanonoate, isopropyl myristhite and octyl stearate); (ii) ether-esters such as fatty acid esters of ethoxylated saturated fatty alcohols; (iii) polyhydric alcohol esters (e.g., ethylene glycol mono and di-fatty acid esters; diethylene glycol mono and di-fatty acid esters; polyethylene glycol mono- and di-fatty acid esters; propylene glycol mono and di-fatty acid esters; polypropylene glycol monostearate; ethoxylated propylene glycol monostearate; glyceryl mono- and di-fatty acid esters; polyglycerol poly-fatty esters; ethoxylated glyceryl mono-stearate; 1,3-butylene glycol monostearate; 1,3-butylene glycol distearate; polyoxyethylene polyol fatty acid ester; sorbitan fatty acid esters; and polyoxyethylene sorbitan fatty acid esters are satisfactory polyhydric alcohol esters); (iv) wax esters (e.g., beeswax, spermaceti wax and tribehenin wax); (v) sugar ester or fatty acids (e.g., sucrose polybehenate and sucrose polycottenseedate); (vi) natural ester emollients include those based on mono-, di- and tri-glycerides (e.g., sunflower seed oil, coconut oil, cottonseed oil, borage oil, borage seed oil, primrose oil, castor and hydrogenated castor oils, rice bran oil, soybean oil, olive oil, safflower oil, shea butter, jojoba oil and combinations thereof); and (vii) animal derived emollients (e.g., lanolin oil and lanolin derivatives).

Hydrocarbons may include, for example, petrolatum, mineral oil, squalane, squalene, isohexadecane, isododecane, $C_{10-26}$ alkanes, $C_{11-13}$ isoparaffins, polybutenes and mixtures thereof.

Fatty acids may include those having 10 to 36 carbon atoms per molecule (e.g., pelargonic acid, lauric acid, myristic acid, palmitic acid, oleic acid, linoleic acid, linolenic acid, stearic acid, isostearic acid, hydroxy stearic acid and behenic acid).

Fatty acohols may include those having 10 to 36 carbon atoms per molecule (e.g., stearyl alcohol, lauryl alcohol, myristyl alcohol, cetyl alcohol and oleyl alcohol).

Thickeners may include salts (e.g., sodium chloride); acrylates (e.g., acrylates copolymers and crosslinked acrylates); polyacrylamides; cellulose or cellulosic derivatives (e.g., sodium carboxymethylcellulose, hydroxypropyl methylcellulose, hydroxypropyl cellulose, hydroxyethyl cellulose, ethyl cellulose and hydroxyethyl methylcellulose); natural gums (e.g., guar, xanthan, *sclerotium*, carrageenan, pectin); inorganics (e.g., clays such as bentonites and hectorites, fumed silicas, talc, calcium carbonate and silicates such as magnesium aluminum silicate). Amounts of the thickener included in the skin moisturizing formulation may range from 0.0001 to 10 wt % (preferably, 0.001 to 1 wt %; more preferably, 0.01 to 0.5 wt %), based on weight of the skin moisturizing formulation.

Preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups. More preferably, the method of making a skin moisturizing formulation of the present invention, comprises selecting a skin moisturizing agent based on its ability to absorb and retain water, wherein the skin moisturizing agent selected is a cationic dextran polymer, comprising a dextran polymer functionalized with quaternary ammonium groups; wherein the skin moisturizing agent has a Kjeldahl nitrogen content corrected for ash and volatiles, TKN, of 0.5 to 4.0 wt % (preferably, 0.75 to 3.25 wt %; more preferably, 0.9 to 2.6 wt %; most preferably, 1.0 to 2.0 wt %) (measured using a Buchi KjelMaster K-375 automated analyzer, corrected for volatiles and ash measured as described in ASTM method D-2364).

Preferably, the method of making a skin moisturizing formulation of the present invention, comprises selecting a skin moisturizing agent based on its ability to absorb and retain water, wherein the skin moisturizing agent selected is a cationic dextran polymer, comprising a dextran polymer functionalized with quaternary ammonium groups; wherein the dextran polymers has a weight average molecular weight, Mw, of 75,000 to 2,000,000 Daltons (preferably, 100,000 to 1,000,000 Daltons; more preferably, 125,000 to 750,000 Daltons; still more preferably, 130,000 to 600,000 Daltons; most preferably, 145,000 to 525,000 Daltons).

Preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the dextran polymer is a branched chain dextran polymer. More preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the dextran polymer comprises a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages. Most preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the dextran polymer is a branched chain dextran polymer; wherein the branched chain dextran polymer comprises a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages according to formula (i)

(i)

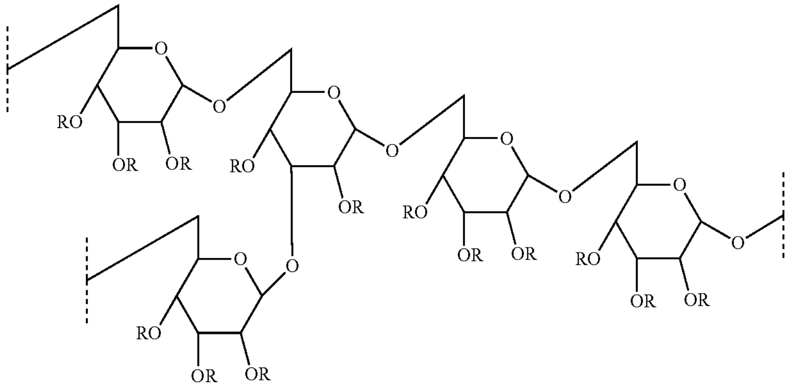

wherein R is selected from a hydrogen, a $C_{1-4}$ alkyl group and a hydroxy $C_{1-4}$ alkyl group; and wherein the average branch off the dextran polymer backbone is <3 anhydroglucose units.

Preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the dextran polymer contain less than 0.01 wt %, based on weight of the dextran polymer, of alternan. More preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the dextran polymer contain less than 0.001 wt %, based on weight of the dextran polymer, of alternan. Most preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the dextran polymer contain less than the detectable limit of alternan.

Preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the quaternary ammonium moieties are selected from the group consisting of at least one of (a) a dextran crosslinking group of formula (A)

(A)

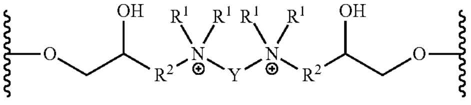

and (b) a quaternary ammonium group of formula (B)

(B)

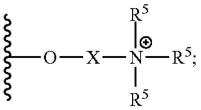

wherein

is a pendant oxygen on the dextran polymer; wherein each $R^1$ is independently selected from a substituted or unsubstituted $C_{1-6}$ alkyl group (wherein "substituted" means that the group in question contains at least one of a halogen, a hydroxy group, an amino group or a carboxy group) (preferably, wherein each $R^1$ is independently selected from an unsubstituted $C_{1-6}$ alkyl group; more preferably, wherein each $R^1$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^1$ is independently selected from the group consisting of a methyl group, an ethyl group, a propyl group, an isopropyl group, a butyl group, an isobutyl group, a tert-butyl group and a sec-butyl group; yet more preferably, wherein each $R^1$ is independently selected from the group consisting of a methyl group, an ethyl group, a propyl group and an isopropyl group; yet still more preferably, wherein each $R^1$ is independently selected from the group consisting of a methyl group and an ethyl group; most preferably, wherein each $R^1$ is a methyl group); wherein each $R^2$ is independently selected from the group consisting of a $C_{1-6}$ alkanediyl group (preferably, wherein each $R^2$ is independently selected from the group consisting of a $C_{1-4}$ alkanediyl group; more preferably, wherein each $R^2$ is independently selected from the group consisting of a $C_{1-2}$ alkanediyl group; most preferably, wherein each $R^2$ is a $-CH_2-$ group); wherein Y is a divalent bridging group (preferably, wherein Y is a divalent bridging group selected from the group consisting of a $C_{1-6}$ alkanediyl group and a $-R^3-O-R^4-$ group; more preferably, wherein Y is a $-R^3-O-R^4-$ group); wherein $R^3$ and $R^4$ are independently selected from the group consisting of a $C_{1-6}$ alkanediyl group (preferably, wherein $R^3$ and $R^4$ are independently selected from the group consisting of a $C_{1-4}$ alkanediyl group; more preferably, wherein $R^3$ and $R^4$ are independently selected from the group consisting of a $C_{1-3}$ alkanediyl group; most preferably, wherein $R^3$ and $R^4$ are both a $-CH_2CH_2-$ group)(preferably, wherein $R^3$ and $R^4$ are the same); wherein X is a divalent linking group bonding the quaternary ammonium moiety to the pendent oxygen on the dextran polymer (preferably, wherein X is selected from divalent hydrocarbon groups, which may optionally be substituted (e.g., with a hydroxy group, an alkoxy group, an ether group); more preferably, wherein X is a $-CH_2CH(OR^6)CH_2-$ group, wherein $R^6$ is selected from the group consisting of a hydrogen and a $C_{1-4}$ alkyl group; most preferably, wherein X is a $-CH_2CH(OH)CH_2-$ group); and wherein each $R^5$ is independently selected from the group consisting of a $C_{1-22}$ alkyl group (preferably, wherein each $R^5$ is independently selected from the group consisting of a $C_{1-3}$ alkyl group and a $C_{6-22}$ alkyl group; more preferably, wherein each $R^5$ is independently selected from the group consisting of a methyl group, an ethyl group and a lauryl group; most preferably, wherein each $R^5$ is a methyl group).

More preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the quaternary ammonium moieties are selected from the group consisting of at least one of (a) a dextran crosslinking group of formula (A) and (b) a quaternary ammonium group of formula (B); wherein the dextran crosslinking group of formula (A) is of Formula (C)

(C)

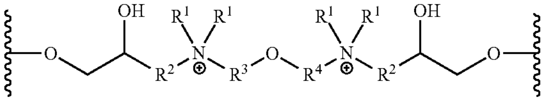

and wherein the quaternary ammonium group of formula (B) is of formula (D)

(D)

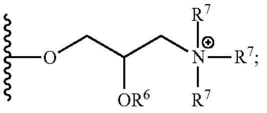

wherein

is a pendant oxygen on the dextran polymer; wherein each $R^1$ is independently selected from a substituted or unsubstituted $C_{1-6}$ alkyl group (wherein "substituted" means that the group in question contains at least one moiety selected from a halogen, a hydroxy group, an amino group or a carboxy group) (preferably, wherein each $R^1$ is independently selected from an unsubstituted $C_{1-6}$ alkyl group; more preferably, wherein each $R^1$ is independently selected from the group consisting of a methyl group, an ethyl group, a propyl group, an isopropyl group, a butyl group, an isobutyl group, a tert-butyl group, a sec-butyl group, a pentyl group, an isopentyl group, a neopentyl group, a hexyl group and an isohexyl group; still more preferably, wherein each $R^1$ is independently selected from the group consisting of a methyl group, an ethyl group, a propyl group, an isopropyl group, a butyl group, an isobutyl group, a tert-butyl group and a sec-butyl group; yet more preferably, wherein each $R^1$ is independently selected from the group consisting of a methyl group, an ethyl group, a propyl group and an isopropyl group; yet still more preferably, wherein each $R^1$ is independently selected from the group consisting of a methyl group and an ethyl group; most preferably, wherein each $R^1$ is a methyl group); wherein each $R^2$ is independently selected from the group consisting of a $C_{1-6}$ alkanediyl group (preferably, wherein each $R^2$ is a $C_{1-4}$ alkanediyl group; more preferably, wherein each $R^2$ is a $C_{1-2}$ alkanediyl group; most preferably, wherein each $R^2$ is a $-CH_2-$ group); wherein $R^3$ and $R^4$ are independently selected from the group consisting of a $C_{1-6}$ alkanediyl group (preferably, wherein $R^3$ and $R^4$ are independently selected from the group consisting of a $C_{1-4}$ alkanediyl group; more preferably, wherein $R^3$ and $R^4$ are independently selected from the group consisting of a $C_{1-3}$ alkanediyl group; most preferably, a $-CH_2CH_2-$ group)(preferably, wherein $R^3$ and $R^4$ are the same); wherein each $R^6$ is selected from the group consisting of a hydrogen and a $C_{1-4}$ alkyl group (preferably, wherein $R^6$ is a hydrogen); and wherein each $R^7$ is independently selected from the group consisting of a methyl group, an ethyl group and a lauryl group (preferably, a methyl group).

Still more preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the quaternary ammonium moieties are selected from the group consisting of at least one of (a) a dextran crosslinking group of formula (A) and (b) a quaternary ammonium group of formula (B); wherein the dextran crosslinking group of formula (A) is selected from the group consisting of

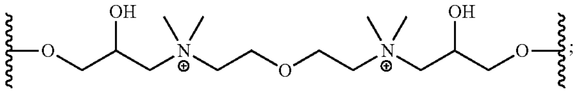
;

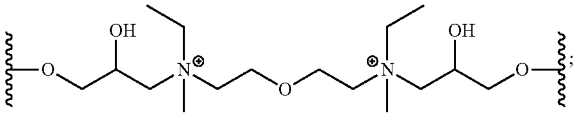
;

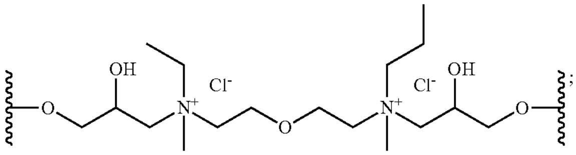
;

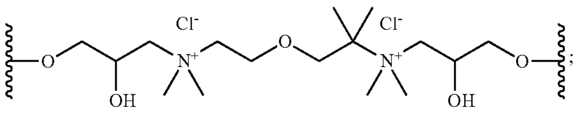
;

and mixtures thereof; and wherein the quaternary ammonium group of formula (B) is of formula (D); wherein

is a pendant oxygen on the dextran polymer; wherein each $R^6$ is selected from the group consisting of a hydrogen and a $C_{1-4}$ alkyl group (preferably, wherein $R^6$ is a hydrogen); and wherein each $R^7$ is independently selected from the group consisting of a methyl group, an ethyl group and a lauryl group (preferably, a methyl group).

Most preferably, the method of making a skin moisturizing formulation of the present invention comprises selecting a skin moisturizing agent based on its ability to absorb and retain moisture, wherein the skin moisturizing agent selected is a cationic dextran polymer, comprising a dextran polymer functionalized quaternary ammonium groups; wherein the quaternary ammonium moieties are selected from the group consisting of (b) a quaternary ammonium group of formula (D); wherein

is a pendant oxygen on the dextran polymer; wherein each $R^6$ is selected from the group consisting of a hydrogen and a $C_{1-4}$ alkyl group (preferably, wherein $R^6$ is a hydrogen); and wherein each $R^7$ is independently selected from the group consisting of a methyl group, an ethyl group and a lauryl group (preferably, a methyl group).

Preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups; wherein the skin moisturizing agent provided comprises <0.001 meg/gram (preferably, <0.0001 meq/gram; more preferably, <0.00001 meq/gram; most preferably, <detectable limit) of aldehyde functionality.

Preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups; wherein the skin moisturizing agent provided comprises <0.1% (preferably, <0.01%; more preferably, <0.001%; most preferably, <detectable limit), of the linkages between individual glucose units in the deposition aid polymer are β-1,4 linkages.

Preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups; wherein the skin moisturizing agent provided comprises <0.1% (preferably, <0.01%; more preferably, <0.001%; most preferably, <detectable limit), of the linkages between individual glucose units in the deposition aid polymer are β-1,3 linkages.

Preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups; wherein the skin moisturizing agent provided comprises <0.001 meq/gram (preferably, <0.0001 meq/gram; more preferably, <0.00001 meq/gram; most preferably, <detectable limit) of silicone containing functionality.

Preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups; wherein the skin moisturizing agent provided comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties. More preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups; wherein the skin moisturizing agent provided comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties; wherein the reactive siloxane is a polymer which may comprise one or more functional moieties selected from the group consisting of amino, amido, alkoxy, hydroxy, polyether, carboxy, hydride, mercapto, sulfate phosphate, and/or quaternary ammonium moieties—these moieties may be attached directly to the siloxane backbone through a bivalent alkylene radical, (i.e., pendant) or may be part of the backbone.

Preferably, the method of making a skin moisturizing formulation of the present invention, comprises selecting a skin moisturizing agent based on its ability to absorb and retain moisture, wherein the skin moisturizing agent selected is a cationic dextran polymer, comprising a dextran polymer functionalized with quaternary ammonium groups; wherein the skin moisturizing formulation formed comprises 0.05 to 10 wt % (preferably, 0.1 to 5 wt %; more preferably, 0.2 to 2.5 wt %; most preferably, 0.35 to 1.5 wt %), based on weight of the skin moisturizing formulation, of the skin moisturizing agent provided.

Preferably, the method of making a skin moisturizing formulation of the present invention, further comprises: providing an additional component selected from the group consisting of an absorbent, an antiaging agent, an antifoaming agent, an antimicrobial agent, an antioxidant (e.g., butylated hydroxytoluene), an antistatic agent, an astringent active, a bioactive agent, a bleaching agent, a dermatologically acceptable personal care cleansing surfactant, a chelating agent, a colorant, a desquamation promoter, an emulsifying agent, an enzyme, a herbal extract, a film forming agent, a foam building agent, a foam booster, a fragrance, a hard particle, an inorganic particle, an oil, an emollient, a humectant, a lubricating agent, a natural ingredient, an opacifier, a pearlizing agent, a chemical or physical exfoliating agent, a penetrant, a pH adjusting agent, a thickener, a pigment, a dye, a plant extract, a preservative (e.g., benzoic acid, sorbic acid, phenoxyethanol), a propellant, a protein/amino acid, a peptide, a salt, a sensory modifier, a silicon feel modifier, a skin lightening agent, an antiacne agent, an antiinflammatory agent, a skin soothing agent, a slip agent, a soap, a soft particle, a suncare agent, a suspending agent, a Vitamin, a wax and mixtures thereof; and combining the additional component with the dermatologically acceptable vehicle and the skin moisturizing agent to form the skin moisturizing formulation.

Preferably, the method of making a skin moisturizing formulation of the present invention, further comprises: providing an antimicrobial agent and combining the antimicrobial agent with the dermatologically acceptable vehicle and the skin moisturizing agent to form the skin moisturizing formulation. More preferably, the method of making a skin moisturizing formulation of the present invention, further comprises: providing an antimicrobial agent and combining the antimicrobial agent with the dermatologically acceptable vehicle and the skin moisturizing agent to form the skin moisturizing formulation; wherein the antimicrobial agent is selected from the group consisting of phenoxyethanol, benzoic acid, benzyl alcohol, sodium benzoate, DMDM hydantoin, 2-ethylhexyl glyceryl ether and isothiazolinone (e.g., methylchloroisothiazolinone, methylisothiazolinone).

Preferably, the method of making a skin moisturizing formulation of the present invention, further comprises: providing an antioxidant and combining the antioxidant with the dermatologically acceptable vehicle and the skin moisturizing agent to form the skin moisturizing formulation (preferably, wherein the skin moisturizing formulation formed contains 0.000001 to 10 wt %, based on weight of the skin moisturizing formulation, of the antioxidant). More preferably, the method of making a skin cleansing formulation of the present invention, further comprises: providing an antioxidant and combining the antioxidant with the dermatologically acceptable vehicle and the skin moisturizing agent to form the skin moisturizing formulation; wherein the antioxidant is selected from the group consisting of butylated hydroxytoluene, lipoic acid, vitamins, herbal extracts (e.g., green tea), retinoxytrimethylsilane, dehydroepiandrosterone (DHEA) and combinations thereof (preferably, wherein the skin moisturizing formulation formed contains 0.000001 to 10 wt %, based on weight of the skin moisturizing formulation, of the antioxidant).

Preferably, the method of making a skin moisturizing formulation of the present invention, further comprises: providing an astringent active and combining the astringent active with the dermatologically acceptable vehicle and the skin moisturizing agent to form the skin moisturizing formulation (preferably, wherein the skin moisturizing formulation formed contains 0.5 to 50 wt %, based on weight of the skin moisturizing formulation, of the astringent active). More preferably, the method of making a skin moisturizing formulation of the present invention, further comprises: providing an astringent active and combining the astringent active with the dermatologically acceptable vehicle and the skin moisturizing agent to form the skin moisturizing formulation (preferably, wherein the skin moisturizing formulation formed contains 0.5 to 50 wt %, based on weight of the skin moisturizing formulation, of the astringent active); wherein the astringent active is selected from the group consisting of alcohol, citric acid, salicylic acid, alpha hydroxy acid, beta hydroxy acid AHA acid, witch hazel, rose water, aloe vera, other herbal extracts, aluminum chlorohydrate, aluminum chlorhydrex, aluminum zirconium chlorhydrex glycine, aluminum sulfate, zinc sulfate, zirconium and aluminum chlorohydroglycinate, zirconium hydroxychloride, zirconium and aluminum lactate, zinc phenolsulfonate and mixtures there.

Preferably, the method of making a skin moisturizing formulation of the present invention, further comprises: providing a dermatologically acceptable personal care cleansing surfactant and combining the dermatologically acceptable personal care cleansing surfactant with the dermatologically acceptable vehicle and the skin moisturizing agent to form the skin moisturizing formulation (preferably, wherein the skin moisturizing formulation formed contains 0.01 to 80 wt % (preferably, 5 to 50 wt %; more preferably, 7.5 to 35 wt %; most preferably, 10 to 20 wt %), based on weight of the skin moisturizing formulation, of the dermatologically acceptable personal care cleansing surfactant). More preferably, the method of making a skin moisturizing formulation of the present invention, further comprises: providing a dermatologically acceptable personal care cleansing surfactant and combining the dermatologically acceptable personal care cleansing surfactant with the dermatologically acceptable vehicle and the skin moisturizing agent to form the skin moisturizing formulation (preferably, wherein the skin moisturizing formulation formed contains 0.01 to 80 wt % (preferably, 5 to 50 wt %; more preferably, 7.5 to 35 wt %; most preferably, 10 to 20 wt %), based on weight of the skin moisturizing formulation, of the dermatologically acceptable personal care cleansing surfactant); wherein the dermatologically acceptable personal care cleansing surfactant is selected from the group consisting of alkyl polyglucosides (e.g., lauryl glucoside, coco-glucoside, decyl glucoside), glycinates (e.g., sodium cocoyl glycinate), glycolipids (e.g., sophorolipids, rhamolipids), sultaines, surfactins, betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof.

Preferably, the method of making a skin moisturizing formulation of the present invention, further comprises: providing a colorant and combining the colorant with the dermatologically acceptable vehicle and the skin moisturizing agent to form the skin moisturizing formulation (preferably, wherein the skin moisturizing formulation formed contains 0.05 to 5 wt % (preferably, 0.1 to 3 wt %), based on weight of the skin moisturizing formulation, of the colorant).

Preferably, the method of making a skin moisturizing formulation of the present invention, further comprises: providing a desquamation promoter and combining the desquamation promoter with the dermatologically acceptable vehicle and the skin moisturizing agent to form the skin moisturizing formulation (preferably, wherein the skin moisturizing formulation formed contains 0.01 to 15 wt %, based on weight of the skin moisturizing formulation, of the desquamation promoter). More preferably, the method of making a skin moisturizing formulation of the present invention, further comprises: providing a desquamation promoter and combining the desquamation promoter with the dermatologically acceptable vehicle and the skin moisturizing agent to form the skin moisturizing formulation (preferably, wherein the skin moisturizing formulation formed contains 0.01 to 15 wt %, based on weight of the skin moisturizing formulation, of the desquamation promoter); wherein the desquamation promoter is selected from the group consisting of alpha-hydroxycarboxylic acids and beta-hydroxycarboxylic acids and mixtures thereof (e.g., glycolic acid, lactic acid, malic acid, salicylic acid and mixtures thereof). These acids may be present as free acid or as salts and $C_{1-30}$ alkyl or aryl esters thereof and lactones generated from removal of water to form cyclic or linear lactone structures.

Preferably, the method of making a skin moisturizing formulation of the present invention, further comprises: providing an enzyme and combining the enzyme with the dermatologically acceptable vehicle and the skin moisturizing agent to form the skin moisturizing formulation. More preferably, the method of making a skin moisturizing formulation of the present invention, further comprises: providing an enzyme and combining the enzyme with the dermatologically acceptable vehicle and the skin moisturizing agent to form the skin moisturizing formulation; wherein the enzyme is selected from the group consisting of amylase, oxidase, protease, lipase and mixtures thereof.

Preferably, the method of making a skin moisturizing formulation of the present invention, further comprises: providing an herbal extract and combining the herbal extract with the dermatologically acceptable vehicle and the skin moisturizing agent to form the skin moisturizing formulation. More preferably, the method of making a skin moisturizing formulation of the present invention, further comprises: providing an herbal extract and combining the herbal extract with the dermatologically acceptable vehicle and the skin moisturizing agent to form the skin moisturizing formulation; wherein the herbal extract is selected from the group consisting of green tea, soy, rice, yarrow, almond, chamomile, licorice, aloe vera, grape seed, citrus unshui, willow bark, sage, thyme, rosemary, pomegranate and mixtures thereof.

Preferably, the method of making a skin moisturizing formulation of the present invention, further comprises: providing fragrance and combining the fragrance with the dermatologically acceptable vehicle and the skin moisturizing agent to form the skin moisturizing formulation (preferably, wherein the skin moisturizing formulation formed contains 0.000001 to 10 wt % (preferably, 0.00001 to 5 wt %; more preferably, 0.0001 to 2 wt %), based on weight of the skin moisturizing formulation, of the fragrance). More preferably, the method of making a skin moisturizing formulation of the present invention, further comprises: providing fragrance and combining the fragrance with the dermatologically acceptable vehicle and the skin moisturizing agent to form the skin moisturizing formulation (preferably, wherein the skin moisturizing formulation formed contains 0.000001 to 10 wt % (preferably, 0.00001 to 5 wt %; more preferably, 0.0001 to 2 wt %), based on weight of the skin moisturizing formulation, of the fragrance); wherein the fragrance is selected from the group consisting of terpenes and terpene derivatives (e.g., myrcene, dihydromyrcenol, citral, tagetone, cis-geranic acid, citronellic acid, aldehydes, alcohols, esters, ketons, natural fragrances (e.g., essential oils), derivatives thereof, mixtures thereof and the like).

Preferably, the method of making a skin moisturizing formulation of the present invention, further comprises: providing a humectant and combining the humectant with the dermatologically acceptable vehicle and the skin moisturizing agent to form the skin moisturizing formulation. More preferably, the method of making a skin moisturizing formulation of the present invention, further comprises: providing a humectant and combining the humectant with the dermatologically acceptable vehicle and the skin moisturizing agent to form the skin moisturizing formulation; wherein the humectant is selected from the group consisting of glycerin, sorbitol, xylitol, maltitol, honey, monoglycerides, lecithins, hyaluronic acid, sodium hyaluronate, urea, allantoin, alpha hydroxy acids, sodium PCA, hydrolyzed wheat/baobab/rice proteins, amino acids, chitosan, seaweed, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, polymeric polyols, cationic polymeric polyols, cationic polymers, starches, celluloses and mixtures thereof.

Preferably, the method of making a skin moisturizing formulation of the present invention, further comprises: providing a pH adjusting agent and combining the pH adjusting agent with the dermatologically acceptable vehicle and the skin moisturizing agent to form the skin moisturizing formulation. More preferably, the method of making a skin moisturizing formulation of the present invention, further comprises: providing a pH adjusting agent and combining the pH adjusting agent with the dermatologically acceptable vehicle and the skin moisturizing agent to form the skin moisturizing formulation; wherein the pH of the skin moisturizing formulation is adjusted to a pH of 4.5 to 9 (preferably, 5 to 8; most preferably, 6 to 7). Most preferably, the method of making a skin moisturizing formulation of the present invention, further comprises: providing a pH adjusting agent and combining the pH adjusting agent with the dermatologically acceptable vehicle and the skin moisturizing agent to form the skin moisturizing formulation; wherein the pH of the skin moisturizing formulation is adjusted to a pH of 4.5 to 9 (preferably, 5 to 8; most preferably, 6 to 7); and wherein the pH adjusting agent is selected from the group consisting of citric acid, lactic acid, hydrochloric acid, aminoethyl propanediol, triethanolamine, monoethanolamine, sodium hydroxide, potassium hydroxide, amino-2-methyl-1-propanol.

Preferably, the method of making a skin moisturizing formulation of the present invention, further comprises: providing a preservative and combining the preservative with the dermatologically acceptable vehicle and the skin moisturizing agent to form the skin moisturizing formulation (preferably, wherein the skin moisturizing formulation formed contains 0.01 to 2 wt %, based on weight of the skin moisturizing formulation, of the preservative). More preferably, the method of making a skin moisturizing formulation of the present invention, further comprises: providing a preservative and combining the preservative with the dermatologically acceptable vehicle and the skin moisturizing agent to form the skin moisturizing formulation (preferably, wherein the skin moisturizing formulation formed contains 0.01 to 2 wt %, based on weight of the skin moisturizing formulation, of the preservative); wherein the preservative is selected from the group consisting of phenoxyethanol, methyl paraben, propyl paraben, imidazolidinyl urea, benzoic acid and its salts, sorbic acid and its salts, phenoxethanol, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol.

Preferably, the method of making a skin moisturizing formulation of the present invention, further comprises: providing a skin lightening agent and combining the skin lightening agent with the dermatologically acceptable vehicle and the skin moisturizing agent to form the skin moisturizing formulation (preferably, wherein the skin moisturizing formulation formed contains 0.1 to 10 wt % (preferably, 0.5 to 2 wt %), based on weight of the skin moisturizing formulation, of the skin lightening agent). More preferably, the method of making a skin moisturizing formulation of the present invention, further comprises: providing a skin lightening agent and combining the skin lightening agent with the dermatologically acceptable vehicle and the skin moisturizing agent to form the skin moisturizing formulation (preferably, wherein the skin moisturizing formulation formed contains 0.1 to 10 wt % (preferably, 0.5 to 2 wt %), based on weight of the skin moisturizing formulation, of the skin lightening agent); wherein the skin lightening agent is selected from the group consisting of plant extracts (e.g., licorice extract, bearberry extract), alpha hydroxy acids, niacinamide, arbutin, azelaic acid, kojic acid, ferulic acid, 12-hydroxystearic acid, hydroquinone, retinol, retinoids, resorcinol and derivatives including 4-substituted resorcinols and mixtures thereof.

Preferably, the method of making a skin moisturizing formulation of the present invention, further comprises: providing a soap and combining the soap with the dermatologically acceptable vehicle and the skin moisturizing agent to form the skin moisturizing formulation. More preferably, the method of making a skin moisturizing formulation of the present invention, further comprises: providing a soap and combining the soap with the dermatologically acceptable vehicle and the skin moisturizing agent to form the skin moisturizing formulation; wherein the soap is selected from the group consisting of sodium stearate, sodium laurate, sodium tallowate, sodium palmitate, potassium stearate, potassium laurate, potassium tallowate, potassium palmitate and mixtures thereof.

Preferably, the method of making a skin moisturizing formulation of the present invention, further comprises: providing a suncare agent and combining the suncare agent with the dermatologically acceptable vehicle and the skin moisturizing agent to form the skin moisturizing formulation (preferably, wherein the skin moisturizing formulation formed contains 0.1 to 30 wt % (preferably, 2 to 20 wt %; more preferably, 4 to 10 wt %), based on weight of the skin moisturizing formulation, of the suncare agent). More preferably, the method of making a skin moisturizing formulation of the present invention, further comprises: providing a suncare agent and combining the suncare agent with the dermatologically acceptable vehicle and the skin moisturizing agent to form the skin moisturizing formulation (preferably, wherein the skin moisturizing formulation formed contains 0.1 to 30 wt % (preferably, 2 to 20 wt %; more preferably, 4 to 10 wt %), based on weight of the skin moisturizing formulation, of the suncare agent); wherein the suncare agent is selected from the group consisting of red petrolatum; titanium dioxide; zinc oxide; 1-(4-methoxyphenol)-3-(4-tert-butylphenyl)propane-1,3-dione; 2-hydroxy-4-methoxybenzophenone; dioxybenzone; sulisobenzone; menthyl anthranilate; para-aminobenzoic acid; amyl paradimethylaminobenzoic acid; octyl para-dimethylaminobenzoate; ethyl 4-bis (hydroxypropyl) para-aminobenzoate; polyethylene glycol (PEG-25) para-aminobenzoate; ethyl 4-bis (hydroxypropyl) aminobenzoate; diethanolamine para-methyoxycinnamate; 2-ethoxyethyl para-methoxycinnamate; ethylhexyl para-methoxycinnamate; octyl para-methoxycinnamate; isoamyl para-methoxycinnamate; 2-ethylhexyl-2-cyano-3,3-diphenyl-acrylate; 2-ethylhexyl-2-cyano-3,3-diphenyl-2-propenoate; 2-ethylhexyl-2-hydroxybenzoate; homomenthyl salicylate; glyceryl aminobenzoate; triethanolamine salicylate; digalloyl trioleate; lawsone with dihydroxyacetone; 2-phenylbenzimidazole-5-sulfonic acid; 4-methylbenzylidine camphor; avobenzone; triazines; benzotriazoles; vinyl group-containing amides; cinnamic acid amides; sulfonated benzimidazoles); 3,3,5-trimethylcyclohexyl 2-hydroxybenzoate and mixtures thereof.

Preferably, the method of making a skin moisturizing formulation of the present invention, further comprises: providing a vitamin and combining the vitamin with the dermatologically acceptable vehicle and the skin moisturizing agent to form the skin moisturizing formulation (preferably, wherein the skin moisturizing formulation formed contains 0.001 to 10 wt % (preferably, 0.01 to 1 wt %; more preferably, 0.1 to 0.5 wt %), based on weight of the skin moisturizing formulation, of the vitamin) More preferably, the method of making a skin moisturizing formulation of the present invention, further comprises: providing a vitamin and combining the vitamin with the dermatologically acceptable vehicle and the skin moisturizing agent to form the skin moisturizing formulation (preferably, wherein the skin moisturizing formulation formed contains 0.001 to 10 wt % (preferably, 0.01 to 1 wt %; more preferably, 0.1 to 0.5 wt %), based on weight of the skin moisturizing formulation, of the vitamin); wherein the vitamin is selected from the group consisting of Vitamin A (retinol), Vitamin B (niacinamide), Vitamin C, Vitamin E, Folic Acid, Biotin, derivatives thereof (e.g., ascorbyl tetraisopalmitate, magnesium ascorbyl phosphate, ascorbyl glycoside, tocopheryl acetate, tocopheryl palmitate, tocopheryllinoleate, DL-panthenol) and mixtures thereof.

Preferably, the skin moisturizing formulation prepared according to the method of making a skin moisturizing formulation of the present invention comprises <0.0001 wt % (more preferably, <0.00001 wt %; more preferably, <detectable limit) of a metal chelator selected from the group consisting of (i) a metal chelator comprising amino groups and at least 5 carboxylate groups; (ii) a metal chelator comprising amino groups and at least 4 phosphonate groups; and (iii) a mixture of (i) and (ii).

Preferably, the method for moisturizing skin (preferably, for reducing visibility of fine lines and wrinkles) of the present invention comprises: providing a skin moisturizing formulation prepared according to the method of making a skin moisturizing formulation of the present invention; and applying the skin moisturizing formulation to the skin of a mammal (preferably, wherein the skin is dry skin; preferably, wherein the skin of a mammal is human skin).

Some embodiments of the present invention will now be described in detail in the following Examples.

Example S1: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with a 21.4 wt % aqueous solution of dextran (132.6 g; Dextran Products Limited) and deionized water (10.0 g). The addition funnel was charged with a 70% aqueous solution of glycidyl trimethylammonium chloride (27.23 g; QUAB® 151 available from SKW QUAB Chemicals). The flask contents were allowed to stir. While the contents were stirring, the apparatus was purged with nitrogen to displace any oxygen entrained in the system. The nitrogen flow rate was about 1 bubble per second. The mixture was purged with nitrogen while stirring for one hour. Using a plastic syringe, a 25% aqueous sodium hydroxide solution (4.77 g) was added over a period of a few minutes to the flask contents with stirring under nitrogen. The flask contents were then allowed to stir under nitrogen for 30 minutes. The contents of the addition funnel were then charged to the flask contents dropwise over five minutes under nitrogen with continued stirring. After the contents of the addition funnel were transferred to the flask contents, the mixture was allowed to stir for 5 minutes. Then heat was applied to the flask contents with a heating mantle controlled using the J-KEM controller set at 55° C. The flask contents were heated to and maintained at 55° C. for 105 minutes. The flask contents were then cooled to room temperature while maintaining a positive nitrogen pressure in the flask. When the flask contents reached room temperature, glacial acetic acid (3.00 g) was added dropwise to the flask contents via a syringe and the mixture was stirred for 10 minutes. The polymer was recovered by non-solvent precipitation of this aqueous solution with methanol. A Waring blender was charged with methanol (700 mL) and polymer solution (20 mL) was slowly added and continuously added at a moderate mixing speed. At the on-set of opacification of the methanol non-solvent, the precipitated polymer was recovered by filtration through a set of nested #40 and #80 US standard sieve screens. The Waring blender was charged with fresh methanol and the non-solvent precipitation of the remaining aqueous polymer solution continued. The polymer collected was briefly air dried, then dried overnight in vacuo at 50° C. The product cationic dextran polymer was a white solid (35.0 g), with a volatiles content of 4.45%, an ash content of 1.85% (as sodium chloride). The volatiles and ash were measured as described in ASTM method D-2364. The Kjeldahl nitrogen content was measured using a Buchi KjelMaster K-375 automated analyzer, and was found to be 1.827% (corrected for volatiles and ash), which corresponds to a trimethylammonium degree of substitution of 0.263.

In-vitro Humectancy

The in-vitro humectancy of materials was evaluated using the following procedure:

1. Weigh the blank aluminum dish and record the weight as $W_0$.
2. Weigh 2.0 g of material for testing into the aluminum dish, and record the combined weight of the material and the aluminum dish as $W_1$.
3. Put the aluminum dish containing the material for testing in an oven preheated at 105° C. for 3 hours.
4. After 3 hours, remove from the oven and immediately weight the aluminum dish containing the material to be tested as $W_2$.
5. Put the aluminum dish containing the material to be tested into a constant temperature & humidity first testing chamber at 45° C. and 90% relative humidity for 40 hours.
6. After 40 hours, remove from the first testing chamber and immediately weight the aluminum dish containing the material to be tested as $W_3$.
7. Put the aluminum dish containing the material to be tested in a constant temperature & humidity second testing chamber at 22° C. and 55% relative humidity, and record the weight of the aluminum dish containing the material to be tested every hour for seven or eight hours as $W_4$, $W_5$, $W_6$, $W_7$, $W_8$, $W_9$, $W_{10}$ and $W_{11}$, respectively.

Calculations from the measured values include:

Weight of the fresh sample of material=$W_1-W_0$

Weight of dry sample=$W_2-W_0$

Weight of sample saturated with water=$W_3-W_0$

Maximum of absorbed water after 0 hour (in %)=100*$[(W_3-W_0)/(W_2-W_0)]$

Remaining absorbed water after 1 hour (in %)=100*$[(W_4-W_0)/(W_2-W_0)]$

Remaining absorbed water after 2 hours (in %)=100*$[(W_5-W_0)/(W_2-W_0)]$

Remaining absorbed water after 3 hours (in %)=100*$[(W_6-W_0)/(W_2-W_0)]$

Remaining absorbed water after 4 hours (in %)=100*$[(W_7-W_0)/(W_2-W_0)]$

Remaining absorbed water after 5 hours (in %)=100*$[(W_8-W_0)/(W_2-W_0)]$

Remaining absorbed water after 6 hours (in %)=100*$[(W_9-W_0)/(W_2-W_0)]$

Remaining absorbed water after 7 hours (in %)=100*$[(W_{10}-W_0)/(W_2-W_0)]$

The higher the wt % or water absorption and the slower the release of water to the atmosphere, the better the humectancy capability of the tested material. The results of the in-vitro humectancy tests for the polymer produced according to Example S1 are compared with those obtained for two benchmark materials in TABLES 1 AND 2.

TABLE 1

| | | Measured Weights | | |
|---|---|---|---|---|
| Variable | Hours | Example S1 | Bench Mark 1[a] | Bench Mark 2[b] |
| $W_0$ | NA | 2.202 | 2.227 | 2.199 |
| $W_1$ | NA | 4.237 | 4.236 | 4.289 |
| $W_2$ | NA | 4.068 | 4.078 | 4.131 |
| $W_3$ | 0 | 5.241 | 5.679 | 5.756 |
| $W_4$ | 1 | 4.915 | 5.270 | 5.312 |
| $W_5$ | 2 | 4.829 | 5.059 | 5.083 |
| $W_6$ | 3 | 4.744 | 4.892 | 4.921 |
| $W_7$ | 4 | 4.693 | 4.777 | 4.813 |
| $W_8$ | 5 | 4.653 | 4.697 | 4.743 |
| $W_9$ | 6 | 4.627 | 4.658 | 4.708 |
| $W_{10}$ | 7 | 4.585 | 4.616 | 4.680 |

[a]Hybloom™ sodium hyaluronate having a molecular weight of 1 MDa to 1.8 MDa available from Bloomage Biotechnology USA Inc.

[b]Hybloom™ sodium hyaluronate having a molecular weight of 10 kDa to 1.0 MDa available from Bloomage Biotechnology USA Inc.

TABLE 2

| | Moisture remaining in starting 100 g sample dry weight material (in %) | | |
|---|---|---|---|
| Hour | Example S1 | Bench Mark 1[a] | Bench Mark 2[b] |
| 0 | 172.35 | 186.48 | 184.09 |
| 1 | 145.39 | 164.38 | 161.08 |
| 2 | 140.78 | 153.02 | 149.24 |
| 3 | 136.23 | 143.98 | 140.85 |
| 4 | 133.48 | 137.76 | 135.28 |
| 5 | 131.33 | 133.43 | 131.67 |
| 6 | 129.92 | 131.35 | 129.86 |
| 7 | 127.71 | 129.06 | 128.39 |

[a]Hybloom™ sodium hyaluronate having a molecular weight of 1 MDa to 1.8 MDa available from Bloomage Biotechnology USA Inc.

[b]Hybloom™ sodium hyaluronate having a molecular weight of 10 kDa to 1.0 MDa available from Bloomage Biotechnology USA Inc.

We claim:

1. A method for making a skin moisturizing formulation, comprising:

providing a dermatologically acceptable vehicle;

selecting a skin moisturizing agent based on its ability to absorb and retain moisture, wherein the skin moisturizing agent selected is a cationic dextran polymer, which has a dextran polymer backbone functionalized with quaternary ammonium groups;

providing the selected skin moisturizing agent;

combining the dermatologically acceptable vehicle and the skin moisturizing agent to form a skin moisturizing formulation; wherein the selected skin moisturizing formulation contains 0.05 to 10 wt %, based on weight of the skin moisturizing formulation, of the skin moisturizing agent; wherein the skin moisturizing formulation is a leave on skin care formulation selected from the group consisting of a color cosmetic, a lotion, a sunscreen and a cream;

wherein the dermatologically acceptable vehicle is selected from the group consisting of an aqueous emulsion; wherein the selected skin moisturizing agent has a Kjeldahl nitrogen content corrected for ash and volatiles, TKN, of 1.0 to 4.0 wt %; wherein the dextran polymer is a branched chain dextran polymer and wherein the dextran polymer has a weight average molecular weight of 145,000 to 525,000 Daltons.

2. A skin moisturizing formulation prepared according to the method of claim 1.

* * * * *